United States Patent
Ghosal

(10) Patent No.: US 6,713,092 B1
(45) Date of Patent: Mar. 30, 2004

(54) WITHANIA SOMNIFERA COMPOSITION, METHOD FOR OBTAINING SAME AND PHARMACEUTICAL, NUTRITIONAL AND PERSONAL CARE FORMULATIONS THEREOF

(75) Inventor: Shibnath Ghosal, Calcutta (IN)

(73) Assignees: Natreon Inc., New Brunswick, NJ (US); Indian Herbs Research & Supply Company Ltd., Saharanpur (IN)

( * ) Notice: Subject to any disclaimer, the term of this patent is extended or adjusted under 35 U.S.C. 154(b) by 0 days.

(21) Appl. No.: 10/308,714

(22) Filed: Dec. 3, 2002

(51) Int. Cl.⁷ .................................. A61K 35/78
(52) U.S. Cl. .................. 424/725; 424/773; 424/774
(58) Field of Search ................................. 424/725, 773, 424/774

(56) References Cited

U.S. PATENT DOCUMENTS 6,153,198 A * 11/2000 Ghosal

OTHER PUBLICATIONS

Anjaneyulyu et al. (Indian Journal of Chemistry (1997), vol., 36B, pp. 161–165).*

* cited by examiner

*Primary Examiner*—Francisco Prats
*Assistant Examiner*—Susan D. Coe
(74) *Attorney, Agent, or Firm*—Walter Katz

(57) ABSTRACT

This invention relates to a composition of the plant Withania Somnifera, and, more particularly to a high purity extract composition with advantageous levels of withanolide glycosides and oligosaccharides, a minimum of polysaccharides, and substantially low levels of free withaferin A and equivalents (withanolide aglycones), which composition provides enhanced cognition-enhancing effects for the user, and an extraction process for obtaining such composition, as well as pharmaceutical, nutritional and personal care use products thereof.

1 Claim, No Drawings

WITHANIA SOMNIFERA COMPOSITION, METHOD FOR OBTAINING SAME AND PHARMACEUTICAL, NUTRITIONAL AND PERSONAL CARE FORMULATIONS THEREOF

CROSS-REFERENCE TO RELATED U.S. PATENT APPLICATIONS

This application is related to U.S. Pat. No. 6,153,198, issued Nov. 28, 2000, to the same applicant as herein.

BACKGROUND OF THE INVENTION

1. Field of the Invention

This invention relates to a composition of the plant Withania Somnifera, and, more particularly to a high purity extract composition with advantageous levels of withanolide glycosides and oligosaccharides, a minimum of polysaccharides, and substantially low levels of free withaferin A and equivalents (withanolide aglycones), which composition provides enhanced cognition-enhancing effects for the user, and an extraction process for obtaining such composition, as well as pharmaceutical, nutritional and personal care use products thereof.

2. Description of the Prior Art

The plant Withania Somnifera Dunn. (Solanaceae), commonly known as Ashwagandha, has been used in herbal formulations of the Ayurvedic or Indian system of medicine to attenuate a cerebral function deficit in the geriatric population, and to augment the faculty of learning and memory to provide a non-specific host defense. These beneficial effects help the organism to ward off stress and act as an adaptogen. Ashwagandha also shows significant protection against pentylene tetrazole—induced seizures in experimental models of epilepsy, indicating its potential utility for treatment of petitmal epilepsy. Ashwagandha administration also produces a decrease in the core body temperature suggesting a reduced Body Metabolic Rate (BMR), enhanced body growth and increased longevity.

Typically, commercially available extracts of Ashwagandha obtained from old roots stock are either completely devoid of sitoindosides, or contain only traces of sitoindosides admixed with large amounts of toxic metabolites of withanolide aglycones, and polysaccharides, and wherein the polyoxygenated withasteroids are degraded during conventional extract procedures.

Accordingly, it is an object of this invention to provide a new and improved Withania Somnifera extract composition, having an enhanced level of withanolide glycosides and oligosaccharides, and minimum amounts of polysaccharides and free withaferin A (aglycone), and an improved extraction process for obtaining such compositions.

SUMMARY OF THE INVENTION

What is described herein is a high purity, substantially water soluble, extract of the Withania Somnifera plant, including its roots and leaves, obtained by a defined extraction procedure, in the form of a stable, free-flowing, light yellow-to-brown herbaceous powder composition, which provides enhanced cognition and augmented learning facility when taken in a dosage of about 100–800 mg/day. The biologically-enhancing composition of the invention includes, by weight, (a) at least 8%, preferably to 25%, of withanolide glycosides and sitoindosides, (b) at least 25%, preferably to 75%, of oligosaccharides, preferably having a mol. wt of <2000, and (c) less than 2%, preferably less than 1% of free withaferin A (aglycone). The high levels of oligosaccharides in the composition further reduces any toxic effect of free withaferin A therein.

Pharmaceutical, nutritional and personal care use formulations thereof also are described.

DETAILED DESCRIPTION OF THE INVENTION

Suitably, the extract composition of the invention is obtained by (a) providing root and leaf stock, in a suitable ratio of each, e.g. 1:1, of a Withania Somnifera plant, preferably which is about 1 to 2 years old, (b) extracting the root and leaf stock substantially immediately at about 60° C. with an aqueous-alcoholic solvent, such as water and methanol, ethanol or isopropyl alcohol, in a suitable ratio, e.g. 1:9, preferably with about 0.1–20% of an additive or *exogenous saccharide* such as dextrin, cane sugar, the plants oligosaccharide, β-cyclodextrin, and the like, to convert the conjugation of free withananolides in the leaves into desirable bioactive wihanolide glycoside; and to enhance the stability of the extract; (c) concentrating the extract under vacuum, (d) treating the residue with an aprotic organic solvent, e.g. chloroform, ethyl acetate, etc. to remove withanolide aglycones therefrom, (e) vacuum drying the insoluble residue below about 60° C., or spray drying, to provide a dry solid, and (f) pulverizing the solid under controlled temperature and humidity conditions.

The aprotic solvent soluble fraction of the extraction process, e.g. chloroform, which contains mainly cytotoxic withanolide aglycones and other constituents of the plant, which do not contribute to the bioactivity of the Ashwagandha composition, can be discarded, if desired.

The aqueous-alcoholic soluble, chloroform-insoluble residue contains withanolide glycoside and sitoindoside components which are potent bioactive constituents of Ashwagandha.

The resultant extract powder also contains very high levels of oligosaccharides which act as a carrier for the bioactive withanolide glycosides. Specifically, this extract (see Table 1, column 2) contains at least 25%, preferably up to 75%, of oligosaccharides, which enhance the bioactivity of the withanolide glycosides. High molecular weight saccharides which decrease its bioactivity i.e. polysaccharides, are present in only small amounts herein.

The composition of the extract compositions of this invention are summarized in Tables 1 and 2 below.

TABLE 1

Standardized Withania Somnifera Extract Powder

| ANALYSIS | SPECIFICATION | RESULTS |
| --- | --- | --- |
| Identity (IR) | HPLC - PDA spectrum | Confirms |
| i) Total withanolide glycoside conjugates (By HPLC) | ≧8% | 12.7% |
| ii) Oligosaccharides (By HPTLC) | ≧25% | 36.3% |
| iii) Free withaferin A and Equivalents - withanolide aglycones (By HPLC) | ≦2.0% | 1.60% |
| Heavy Metals (as PB) | ≦0.002% | Complies |
| Arsenic (As) | ≦0.0002% | Complies |
| Sulfated Ash | ≦8% | Complies |
| Moisture content | ≦5% | 3.50% |

TABLE 1-continued

Standardized Withania Somnifera Extract Powder

| ANALYSIS | SPECIFICATION | RESULTS |
|---|---|---|
| Microbiological Tests | | |
| Total Aerobic plate count | $<10^3/g$ | $2 \times 10^2$ CFU/gm |
| *Escherichia coli* | Absent in 1 g | Ni |
| Salmonella | Absent in 10 g | Nil |
| Ratio of withanolide glycoside conjugates and free withaferin A (aglycones) | 75-95 to 25-5 | 89:11 |
| Ratio of withanolide glycoside conjugates and oligosaccharides | 12-35 to 82-65 | 26:74 |

Product Description

| | |
|---|---|
| Appearance | Fine Powder |
| Color | Brown to brownish green |
| Odor | Charactistic |
| Taste | Mild bitter |
| Water-soluble extractive value | $\geq 80\%$ |

TABLE 2

Effect of Additives on Extraction of Withania Somnifera (Root + Leaf) Extracted with 90% Methanol

| | Additive | | |
|---|---|---|---|
| Sample | Withanolide glycosides (% by w/w) (By HPLC) | Oligosaccharides (% w/w) (By HPTLC) | Free Withaferin (% w/w) (By HPLC) |
| Withania somnifera (Control) | 10.12 | 28.90 | 1.60 |
| Withania somnifera/5% Withania oligosaccharides | 8.99 | 33.63 | 0.67 |
| Withania somnifera/10% Withania oligosaccharides | 11.53 | 25.90 | 1.54 |
| Withania somnifera/0.1% B-cyclodextrin | 10.00 | 42.10 | 1.22 |

HPTLC Analysis of Withania Somnifera Extracts

Withanolide glycosides/sitoindosides, the major bioactive constituents of Withania Somnifera, are not readily identifiable in HPTLC chromatographs. However, upon carefully controlled hydrolysis, where they are converted into withanolide aglycones, these components are readily observed in their HPTLC fingerprints. On the basis of such post-hydrolysis findings, the presence and amounts of such withanolides/sitoindoside glycosides in the extract composition of the invention was determined.

Analytical and Chromatographic Conditions:

| | |
|---|---|
| Plate material: | Silica gel 60F254 |
| Solvent: | n-Butanol/Acetic acid/Water 4/1/2 (b efore hydrolysis) |
| | Chloroform/Methanol 90/10 (after hydrolysis) |
| Application mode: | Camag linomat IV |
| Development mode: | Twin Trough chamber |
| Detection wavelength: | 260 nm |

The withanolide aglycones are highly susceptible to rearrangement under such acidic conditions.

The extract composition of the invention can be formulated into pharmaceutical, personal care and nutritional use compositions as described in the above-mentioned patent. In addition the compositions herein have particular medicinal activities as follows:

Medicinal Activity

One of the most significant characteristics of the Withania somnifera—oligosaccharides compositions is their capacity to form inclusion complexes in which substrates, e.g. withanolide glycosides (-sitoindosides) and aglycones, are sequestered, by way of (i) van der Waals attraction, (ii) hydrogen bonding, (iii) release of solvent water molecules from the cavity, and (iv) release of strain energy in the macrocycles, in the structural cavity. This property, in turn, enhances the systemic absorption of the bioactive molecules because, the resultant interction, in vivo, of the contained compound is substantially modified by the protein proteolytic enzymes of the gastrointestinal tract oligosaccharide surface association, it spans the oligosaccharide-containing sitoindosides from premature metabolism.

In summary, the effectiveness of the WS composition of the invention has been found to be superior to such antistress agents as Panax ginseng (Asian) and Eleutherococus senticosus (Siberian Ginseng). These agents suffer from a number of side effects, whereas the invention composition shows no side effect and no decline in performance even on prolonged use. The invention composition has many applications, including:

A potent adaptogen.

An anti-stress agent.

An immuno-enhancer.

An anti-craving agent of drugs of abuse, tobacco, alcohol.

An anti-oxidant

An anti-aging agent.

Semen and virility-increasing agent.

A Potent Adaptogen

An adaptogen is an agent that elicits adaptive responses manifested by non-specific host resistance, protective actions against diverse forms of stress (static and dynamic) and elevation of immune status of subjects. Long years of pharmacological, chemical, immunological and toxicological researches by Indian scientists have established that selected root extracts of a cultivated chemotype of Withania somnifera Dunn. (Solanaceae), containing a defined combination of withanolide glycosides (-sitoindosides VII–X), aglycone (withaferin-A) as inclusion complex in Withania—oligosaccharides, is a high fidelity agent against different forms of static and dynamic stresses of the body, mind and environment of man.

An Anti-stress Agent

In general, stress is subjective in the response of the organism to the stressor causing environmental stress, heat stress, cold stress, noise stress, stress from toxic chemicals, etc. Response to stress is non-specific and independent of the nature of stressor so that the stress-induced state produced in subjects by diverse stressors is indistinguishable. The anti-stress effect of the composition herein was determined by adopting a battery of tests (stress parameters), e.g. restraint stress, morphineinduced toxicity, adrenocortical activity, in laboratory animals. The invention composition significantly attenuated these stress-induced syndromes ranging from anxiety, depression, thermic changes, gastric ulcers, convulsions, and adrenocortical activation.

Withania Somnifera Extract Composition Evaluated for Anti-Stress Activity in Albino Rats

MATERIALS AND METHODS (i) Animals: Albino rates (Sprague Dowley strain) collected from the Animal House, R&D Centre of Indian Herbs, Saharanpur, were used in the study. The animals were housed in colony cages maintained at an embient temperature of 25° C.±2° C. with 12 hours light and dark cycle. Rats were divided into various groups each containing 6 rats of equal proportions of male and female in each group.

(ii) Drug treatments: Withania somnifera (WS) extracts were used in the study. Extracts were administered orally by dissolving in 0.3% carboxymethyl cellulose (CMC) suspension, using orogastric cannula, to rats at the dose of 100 mg/kg daily for 7 days. Control rats received equal volume of vehicle (0.3% CMC) only.

(iii) Chemicals: The following chemicals were procured and used in the study:
 (A) Methylene chloride (Qualigens fine chemicals, Mumbai, India)
 (B) Dry sodium sulfate (Reidel (India) Chemicals Pvt. Ltd., New Delhi)
 (C) Ethanol (Changshu Yangyuan Chemical, China)
 (D) Corticosterone (Sigma, USA)

(iv) Induction of cold immobilization stress: After oral administration of the extracts or vehicle the rats were slightly anaesthetized with ether. Both lower and upper extremities were fixed together and the rats were wrapped in wooden gaze. They were horizontally suspended in the dark at 4° C. for 4 hours and finally sacrificed in anesthesia (Vogel and Vogel, 1997).

(v) Gastric Ulceration: The stomach was removed and split open along the greater curature. The number of discrete ulcers were noted by the help of a magnifying glass. The severity of the ulcers were scored after histological confirmation (Vogel and Vogel, 1997) as:

| | |
|---|---|
| 0 | = no ulcers |
| 1 | = superficial ulcers |
| 2 | = deep ulcers |
| 3 | = perforation |

An ulcer index $U_1$ is calculated:

| | |
|---|---|
| $U_1$ | $= U_N + U_s + U_p \times 10^{-1}$ |
| $U_N$ | = average of number of ulcer per animal |
| $U_s$ | = average of severity score |
| $U_p$ | = percentage of animals with ulcers |

(vi) Plasma corticosterone estimation: one ml plasma was diluted with 2 ml distilled water and extracted with 5 ml petrol ether to remove the lipids. The petrol ether was discarded. Two ml of the water layer were extracted twice with 5 ml methylene chloride by vigorous shaking for 15 minutes in a glass stoppered tube. The methylene chloride extracts were shaken with 1 ml ice-cold 0.1 N NaOH. The water phase was immediately removed and the methylene chloride extract was mixed with 5 ml of fluorescence reagent (7 parts concentrated sulfuric acid, 3 parts 96% ethanol, v/v) in a glass stoppered tube. After vigorous shaking, the methylene chloride phase was carefully removed and fluorescence was read at 530 nm in a spectroflurometer with excitation wavelength 470 nm and emission wavelength 525 nm. For calibration concentrations of 0.025, 0.05, 0.1, 0.2, 0.4 and 0.8 $\mu$g/ml were treated identically.

RESULTS AND DISCUSSION

Immobilization stress-induced gastric ulcers: WS extracts induced decrease in number and severity of ulcers induced by cold-immobilization stress. WS extract (1:5) was most promising in view of its lowest ulcer index, The results are summarized in Table 3. It is now recognized that the central nervous system plays a significant role in gastric function and stress ulcer formation (Henke, 1990). Thus, the attenuation of immobilization stress-induced ulcers by WS extracts indicated that it has a central locus of action, possibly on the telencephalic limbic system.

Plasma corticosterone estimation: Cold-immobilizaton stress induced an increase in plasma corticosterone concentrations. WS extracts, which have no effect their own on this parameter attenuated the stress effect on this biochemical marker of adrenocortical activity (Table 4). Stress-induced stimulation of the hypothalamo pituitary-adrenocortical axis (HPAA) has been conclusively established. In the present study this effect of cold immobilizabon stress was reflected in increase in plasma corticosterone concentrations, effect known to be produced by augmented synthesis and release of adrenocorticotropin (ACTH).

The results indicate that WS extract (1:5) has maximum anti-stress activity among three WS extracts. The results are summarized in Table 4.

CONCLUSION

All the three WS extracts have showed anti-stress activity in cold-immobilization stress-induced gastric ulcer model and plasma corticosterone concentration in rats. Among three extracts, WS extract (1:5) has shown most promising ant-stress activity. Hence, it may be concluded that WS extract (1:5) has comparatively better ant-stress activity than other extracts, as shown in Tables 3 and 4 below.

TABLE 3

Effect of Withania Somnifera Extracts
on Cold Immobilization Stress in Rats
(Values are expressed as mean of 6 rats in each group)

| Treatment | Chemical Composition | Severity of ulcer scores ($U_s$) | Number of ulcers ($U_N$) | % of animals with ulcer ($U_p$) | Ulcer index ($U_1$) |
|---|---|---|---|---|---|
| Unstressed Control | — | 0.00 | 0.00 | 0.00 | 0.00 |
| Stressed Control (0.3% CMC) | — | 1.67 | 8.33 | 83.33 | 9.33 |
| WS extract (1:5) (100 mg/kg, p.o.) | Withanolide glycosides (8.8%) Oligosaccharides (43.2% | 0.67 | 2.67 | 50.00 | 5.33 |

TABLE 4

Effect of Withania Somnifera Extracts
on Cold Immobilization Stress Induced Changes in
Plasma Corticosterone Levels of Rats
(Values are expressed as mean of 6 rats in each group)

| Treatment (Dose) | Chemical Composition | Plasma Corticosterone (mcg/dl) |
|---|---|---|
| Unstressed control | — | 26.67 |
| Stressed control | — | 106.40 |
| WS extract (1:5) (100 mg/kg, p.o) | Withanolide glycosides (8.8%) Oligosaccharides (43.2%) | 50.67 |

As Immuno-enhancer

Classically, stress responses as determined by increased circulated-glucocorticoid hormone levels, are regulated by the hypothalamic pituitary-adrenal axis via increased production and release of ACTH. Subsequent studies have demonstrated that, under certain circumstances, e.g. leukocyte stimuli, virus-induced immunocyte or leukocyte-derived ACTH, the pituitary gland may not be required for an ACTH-mediated stress response. These and other studies have established immune and neuro-mediated systems represent an integrated circuit that results from a shared set of signal molecules (hormones) and receptors. By improving immune status of man stress syndromes can be alleviated and combated.

An Immunomodulator

In both animal and human studies, the invention composition has shown immunomodulatory effects as revealed by the elicitation and activation of macrophages present in the blood stream, and is more effective than Panax ginseng at eliciting and activating macrophages and components of the immune system. To assess its effect on the activation of the elicited macrophages, the surface Fc receptor expression of the elicited macrophages was determined. The Fc receptor binds the Fc fraction of the antibody. Through the Fc receptors the pentoneal macrophages can bind the target-coated cells. These findings suggest that the macrophages elicited by the composition produce a significant number of super rosettes as compared to those produced by the control (normal) macrophages. The number of small rosettes, on the other hand, were more numerous in the normal macrophages. The increase in the number of super rosettes with a concomitant decrease in the number of the small ones indicated augmented expression of the Fc pr elicited cell of both 4 and 37° C. Interestingly, the lytic potential of the effect or cell population was only marginally increased after treatment. It seems likely, therefore, that the activity of the elicited macrophages was not due to cytotoxicity but to immunomodulation. This was further supported by the decreased tumor growth, while there was only a marginal increase in the number of dead cells in the treated groups.

An important role in the amplification of the non-specific immunological defense is played by lysosomal enzymes secreted by the activated macrophages. The results of the specific activity of anzymes of the tumor-associated macrophages, and the acid phosphatase activity induced by the composition, established significant immunostimulatory effects of the composition.

As an Anti-craving Agent of Drugs of Abuse

The existence of bi-directional circuits between the central nervous system (CNS) and the immune system opens up the possibility that by elevating the immune status of subjects their craving for drugs of abuse can be diminished. Indeed, a direct link between opioid peptides, receptors and immune functions has been established. It has been observed that morphine and other abusive agents have depressed the immune functions of addicts. Chemical constituents present in the invention composition have not only been found to elevate the immune status of recipients but also to act as anticraving-antiamethystic agents.

A Cognition Enhancer

The invention composition has been shown to augment learning acquisition and memory retrieval in deficient recipients. The application composition in the treatment of Alzheimer's disease has also been suggested by recent scientific evaluations. Systemic application have modified acetylcholinesterase (AChE) activity differently in different areas of the brain. These changes are accompanied by enhanced $M_1$-muscarinic cholinergic receptor binding in different areas of the brain. Induced increase in cortical muscarinic acetylcholine capacity explains, at least partly, the cognition-enhancing and memory-improving effects of withania observed in animals and humans. Further, it has also been shown to inhibit the activity of acute phase reactants during inflammation and neurodegeneration produced by neurotoxins.

An Antioxidant

Increased generation of oxidative free radicals and/or impaired antioxidant defense mechanisms have been implicated in the ageing process particularly neurodegenerative conditions, including Parkinsonism and Alzheimer's disease, in chromic stress induced perturbed homeostasis, including immunodepression, inflammation, diabetes mellitus, peptic ulcer and other disease conditions. Major oxidative free radical scavenging enzymes are superoxide dismutase (SOD), catalase (CAT) and glutathione peroxidase (GPX). Deficient functioning of these enzymes leads to accumulation of oxidative free radicals and consequent degenerative changes. Recent studies have shown to increase the cortical and striatal concentrations of the antioxidant enzymes, SOD, CAT and GPX. These studies have further indicated that the increase in the oxidative free radical scavenging activity is responsible, at least partly, for the anti-stress and immunomodulatory effects of this agent.

The composition was given to some 200 patients, in the course of five studies, a period of 11 months, and it showed no adverse side effects. Additionally, a clinical study of the role of Withania somnifera in arthropathhies had shown that it was free from any toxic effect The maximum dose employed was 6 g (root powder in gelatin capsule) day$^{-1}$ for 30 days; it showed no adverse side effect.

Oxidants and antioxidants have well defined functions and reside in specific cellular compartments. An imbalance between oxidants and antioxidants results in many pathophysiological changes. For example, Ultraviolet B (UVB) radiation is believed to be an initiator of lipid peroxidabon, and, in fact, a UVB-dependant generation of hydroxyl radicals and lipid peroxides has been demonstrated in human keratinoxyte and fibroblast cultures. The underlying mechanism appears to be the UVB-induced formation of superoxide radical and its attack on ferritin, resulting in release and mobilizabon of free iron. Furthermore, superoxide can react to hydrogen peroxide, which again restarts the Fenton reaction.

Premature skin aging (photoaging) and carcinogenesis are generally believed to be consequences of chronic ultraviolet radiation (UVR) exposure. Reactive oxygen species (ROS), such as Superoxide and other free radicals and non-radicals deplete the skin of its antioxidant defense; consequently, damage to biomolecules such as lipids, proteins and nucleic acid occurs.

The present inventive composition can also be applied topically to protect skin from premature aging.

USE COMPOSITIONS OF INVENTION

The following examples have not, necessarily, been conducted, but are instead illustrative of the invention.

A. Personal Care

In use, the compositions of Examples 1–4 below improves skin appearance and also to suppress skin aging due to the effects of exposure to sunlight.

EXAMPLE 1

| MOISTURE SKIN CARE LOTION | |
|---|---|
| Ingredients | % (W/W) |
| Part A | |
| Stearic Acid XXX | 10.0 |
| Methyl Salicylate USP | 0.5 |
| Camphor USP | 0.5 |
| PPG-5 Ceteth-10 Phosphate | 2.0 |
| Propyl Paraben | 0.1 |
| Part B | |
| PPG-12 PEG-50 Lanolin | 2.0 |
| Present composition | 0.5 |
| Deionized Water | 84.3 |
| Methyl Paraben | 0.1 |
| Total | 100.00 |

Procedure: Combine ingredients of Part A with mixing and heat to 80–85° C. Combine ingredients of Part B with mixing and heat to 80–85° C. Add Part B to Part A with mixing and cool to desired fill temperature.

EXAMPLE 2

| WATER-IN-OIL COLD CREAM | |
|---|---|
| Ingredients | % (W/W) |
| Part A | |
| Mineral Oil and Lanolin Alcohol | 5.0 |
| Lanolin Alcohol NF | 1.9 |
| Aluminum Stearate, #22 | 0.1 |
| Microcrystalline Wax | 5.0 |
| Ozokerite, 170.degree. C. MP | 2.5 |
| Mineral Oil, 70 ssu | 16.4 |
| Part B | |
| Glycerin | 1.5 |
| Inventive Composition | 1.0 |
| Magnesium Sulfate | 0.7 |
| Deionized Water | 66.7 |
| Part C | |
| Germaben II (1) | 1.0 |
| Total | 100.0 |

Procedure: Combine ingredients of Part A with mixing and heat to 70° C. Combine ingredients of Part B with mixing and heat to 70–75° C. Add Part B to Part A with mixing and cool to 40° C. Add Part C with mixing and cool to desired fill temperature.

EXAMPLE 3

| SKIN REJUVENATING (O/W) LOTION | |
|---|---|
| Ingredients | % (W/W) |
| Phase A | |
| Polyglyceryl-3 Methyl Glucose Distearate | 3.50 |
| Glyceryl Stearate, PEG-100 Stearate | 2.50 |
| Dicapryl ether | 5.00 |
| Coco-Caprylate/Caprate | 5.00 |
| Propylene Glycol Dicaprylate/Dicaprate | 3.00 |
| Almond Oil | 2.00 |
| Cetyl alcohol | 1.50 |
| Inventive Composition | 2.00 |
| Phase B | |
| Glycerin | 3.00 |
| Propylene glycol | 3.00 |
| Allantoin | 0.20 |
| Methylparaben | 0.15 |
| Water, deionized | q.s. |
| Phase C | |
| Phenoxyethanol and Isopropylparaben and Isobutylparaben and Butylparaben | 0.50 |
| Total | 100.00 |

Procedure: Combine A, stir and heat to 65° C. Combine B, stir and heat to 65° C. Add A to B while stirring. Homogenize at moderate speeds to avoid foaming, while allowing mixture temperature to cool to 40° C. Add C, homogenize. Stir gently until mixture is homogeneous.

Example 4 below illustrates the effectiveness of the composition of the invention in enhancing the skin protective effect of sunscreen formulations.

EXAMPLE 4

SUNSCREEN O/W SPRAY-LOTION ESTIMATED SPF 20

| Ingredients | % (W/W) |
|---|---|
| Phase A-1 | |
| Propylene Glycol Isoceteth-3 Acetate | 5.00 |
| Octyl methoxycinnamate | 7.50 |
| Benzophenone-3 | 3.00 |
| Homomenthyl Salicylate | 7.00 |
| Steareth-2 | 0.40 |
| Steareth-10 | 0.80 |
| Acrylates/C.sub. 10–30 Alkyl Acrylate Crosspolymer | 0.18 |
| Synthetic Wax | 0.80 |
| Dimethicone | 1.00 |
| Inventive Composition | 0.25 |
| Phase B | |
| Demineralized water | 50.0 qs |
| Phase C | |
| Demineralized water | 19.82 |
| Phenylbenzimdazole sulfonic acid | 1.00 |
| Propylene glycol | 2.00 |
| Triethanolamine | 0.90 |
| Propylene Glycol and DMDM Hydantoin and Methylparaben | 1.00 |
| Total | 100.00 |

Procedure: Combine A, stir and heat to 80° C. Heat B to 80° C. Add A to B while stirring with a propeller mixer. Continue stirring A/B for 20 minutes while maintaining the temperature between 70–75° C. Combine C, heat and stir to 45° C. until dissolved. Add C to A/B with agitation. Qs water. Gently homogenize A/B/C allowing mixture to cool to room temperature. Adjust pH to 7.1–7.3 with TEA. Use high shear spray device to dispense.

EXAMPLE 5

SKIN LIGHTENING/BRIGHTENING LOTION

| INCI NAME | % w/w |
|---|---|
| Phase A | |
| Water (demineralized) | 56.18 |
| Disodium EDTA | 0.05 |
| Propylene Glycol | 5.00 |
| Xantham Gum | 0.25 |
| Magnesium aluminum stearate | 0.40 |
| Phase B | |
| Cetearyl alcohol and cetearyl glucoside | 7.00 |
| Apricot kernel oil | 10.00 |
| Octyl stearate | 3.00 |
| Dimethicone | 6.00 |
| Inventive Composition | 3.00 |
| Phase C | |
| Water (demineralized) | 10.00 |
| Phase D | |
| Triethanolamine | q.s. |
| Phase E | |
| Phenoxyethanol, Isopropylparaben, Isobutylparaben, Butylparaben | 1.00 |
| Total | 100.00 |

Procedure: Combine A and heat to 70–75° C. Combine B and heat to 70–75° C. Add B to A while stirring. Homogenize until mixture cools to 60° C. and then add phase C. Adjust pH, if necessary with TEA to ~5.0. Add phase E. Mix until uniform.

B. Pharmaceutical and Nutritional Composition

EXAMPLE 6

TABLETS AND CAPSULES OF *WITHANIA SOMNIFERA* INVENTIVE COMPOSITION

| Ingredient | Composition (w/w, in %) | Quantity per tablet (mg) |
|---|---|---|
| 1. Inventive Composition | 60.0 | 250.0 |
| 2. Avicel pH 101 | 20.0 | 84.0 |
| 3. Starch 1500 | 17.5 | 75.5 |
| 4. Steric acid, N.F. (powder) | 2.0 | 8.5 |
| 5. Cab-O-Sil | 0.5 | 2.0 |

Note: *Withania somnifera* extract is granulated with starch paste to make it a free-flowing powder.
Procedure: Blend all the ingredients, except 4, for 25 min. in a blender. Screen in 4 and blend for an additional 5 min. Compress into tablets using 7/16 in standard concave tooling. Alternately, the blended material can be filled into appropriate capsules.

EXAMPLE 7

CHEWABLE TABLETS

| Ingredient | Composition (w/w, in %) | Quantity per tablet (mg) |
|---|---|---|
| 1. Inventive Composition | 10.26 | 27.60 |
| 2. Sodium ascorbate, USP | 36.26 | 81.60 |
| 3. Avicel pH 101 | 19.12 | 38.50 |
| 4. Sodium saccharin, (powder), N.F. | 0.56 | 1.25 |
| 5. DiPac | 29.30 | 66.00 |
| 6. Stearic acid, N.F. | 2.50 | 5.60 |
| 7. Imitation orange Flavor | 1.0 | 2.25 |
| 8. FD & C Yellow #6 dye | 0.5 | 1.12 |
| 9. Cab-O-Sil | 0.5 | 1.12 |

Procedure: Blend all the ingredients, except 6, for 20 min in a blender. Screen in 6 and blend for an additional 5 min. Compress into tablets using 7/16-in standard concave tooling.

EXAMPLE 8

"MAINTENANCE" MULTIVITAMIN TABLETS AND CAPSULES

| Ingredient | Composition (w/w, in %) | Quantity per tablet (mg) |
|---|---|---|
| 1. Vitamin A acetate (dry form 500 IU and 500 D.sub.2 per mg) | 5.5 | 11.0 |
| 2. Thiamine mono-nitrate, USP | 0.8 | 1.65 |
| 3. Riboflavin, USP | 1.1 | 2.10 |
| 4. Pyridoxine HCl, USP | 1.0 | 2.10 |
| 5. 1% Cyanocobalamine (in gelatin) | | |
| 6. D-Calcium pantothenate, USP | 3.75 | 7.50 |
| 7. Inventive Composition, free-flowing | 33.25 | 66.50 |
| 8. Niacinamide | 11.0 | 22.00 |
| 9. DiTab | 13.1 | 26.20 |
| 10. Microcrystalline cellulose, N.F. | 25.0 | 50.00 |
| 11. Talc, USP | 3.0 | 6.00 |
| 12. Stearic acid, (powder), N.F. | 1.5 | 3.00 |
| 13. Magnesium stearate, (powder), N.F. | 1.0 | 2.00 |

Procedure: Blend all ingredients for 20 min in a suitable blender. Screen in 12 and blend for an additional 5 min. Compress at a tablet weight of 200 mg using 3/8-in standard concave tooling. Alternately, blended material is filled into a capsule containing 200 mg of multi-vitamins. These tablets or capsules can be used as nutritional supplements.

EXAMPLE 9

GERIATRIC FORMULA VITAMIN TABLETS

| Ingredient | Composition (w/w, in %) | Quantity per tablet (mg) |
|---|---|---|
| 1. Ferrous sulfate, USP 95% Ethecal granulation | 30.00 | 156.00 |
| 2. Thiamine mono-nitrate, USP | 1.09 | 6.00 |
| 3. Riboflavin, USP | 1.00 | 5.50 |
| 4. Niacinamide, USP | 6.00 | 33.00 |
| 5. Inventive Composition, free-flowing powder | 15.45 | 96.00 |
| 6. Calcium pantothenate, USP | 0.73 | 4.00 |
| 7. Pyridoxine HCl, USP | 0.14 | 0.75 |
| 8. Cyanocobalmine, 0.1% spray dried | 0.82 | 4.50 |
| 9. AcDisol | 2.00 | 11.00 |
| 10. Stearic acid, (powder), N.F. | 2.00 | 11.00 |
| 11. Magnesium stearate, (powder), N.F. | 0.25 | 1.38 |
| 12. CeloCat | 40.52 | 211.87 |

Procedure: Prepare a premix of items 2, 3, 6, 7. Mix in other ingredients except 10 and 11 and blend for an additional 5 min. Compress using oval punches (1 = 0.480 in., w = 0.220.times.cup = 0.040 in.) Sugar or film coat.

EXAMPLE 10

Geriatric Formula Vitamin Tablets

Example 9 was repeated except 50% Inventive composition is replaced with ascorbic add USP fine crystal. These tablets can be used as nutritional supplements.

EXAMPLE 11

BEVERAGE WITH WITHANIA SOMNIFERA STANDARDIZED EXTRACT

| Ingredient No. | Ingredient | Quantity per 500 mL |
|---|---|---|
| 1 | Extract of Invention | 10 mg–2 gm |
| 2 | Excipients: Carbonated Water, Food Starch-Modified, High Fructose Corn Syrup and/or Sucrose and/or Sugar, Sodium Benzoate, Caffeine, Glycerol Ester of Wood resin, Flavors, Colors | q.s |

EXAMPLE 12

CEREAL WITH WITHANIA SOMNIFERA STANDARDIZED EXTRACT

| Ingredient No. | Ingredient | Quantity per 1 Kg |
|---|---|---|
| 1. | Extract of Invention | 500 mg–10 gm |
| 2. | Excipients: Whole Grain Oats, Oat Bran, Sugar, Modified Corn Starch, Brown Sugar Syrup, Salt, Calcium Carbonate, Trisodium Phosphate, Wheat Flour, Vitamin E (Mixed tocopherols), Zinc & Iron (Mineral nutrients), Niacinamide (A B Vitamins), Vitamin B6 (Pyridoxine Hcl), Vitamin B2 (Riboflavin), Vitamin B1 (Thiamin Mononitrate), Vitamin A (Palmitate), Vitamin A B (Folic acid), Vitamin B12, Vitamin D | q.s |

While the invention has been described with particular reference to certain embodiments thereof, it will be understood that changes and modifications may be made which are within the skill of the art Accordingly, it is intended to be bound only by the following claims, in which:

What is claimed is:

1. A process of making an Withania Somnifera extract composition which comprises (a) providing root stock and leaves of a Withania Somnifera plant which is about 1–2 years old, (b) extracting said root stock and leaves with an aqueous-alcoholic solvent in the presence of a exogenous saccharide, c) concentrating the extract under vacuum, (d) treating the residue with an apolar organic solvent to remove free withanolide A aglycones therefrom, (e) vacuum the insoluble residue of such treatment below about 60° C. to provide a dry solid, and (f) pulverizing the solid under controlled temperature and humidity conditions, to obtain the desired powder product.

\* \* \* \* \*